United States Patent
Tanaka et al.

(10) Patent No.: US 10,988,446 B2
(45) Date of Patent: Apr. 27, 2021

(54) CONCISE PROCESS FOR PREPARING 3-PYRROLIDINE CARBOXYLIC ACID DERIVATIVES

(71) Applicant: OKINAWA INSTITUTE OF SCIENCE AND TECHNOLOGY SCHOOL CORPORATION, Okinawa (JP)

(72) Inventors: Fujie Tanaka, Okinawa (JP); Feng Yin, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 0 days.

(21) Appl. No.: 16/321,137

(22) PCT Filed: Sep. 28, 2016

(86) PCT No.: PCT/JP2016/004377
§ 371 (c)(1),
(2) Date: Jan. 28, 2019

(87) PCT Pub. No.: WO2018/025295
PCT Pub. Date: Feb. 8, 2018

(65) Prior Publication Data
US 2019/0169125 A1    Jun. 6, 2019

(30) Foreign Application Priority Data
Aug. 1, 2016  (JP) .............................. JP2016-151249

(51) Int. Cl.
C07D 209/54    (2006.01)
C07D 207/16    (2006.01)
C07C 201/12    (2006.01)
C07C 205/51    (2006.01)

(52) U.S. Cl.
CPC .......... *C07D 209/54* (2013.01); *C07C 201/12* (2013.01); *C07C 205/51* (2013.01); *C07D 207/16* (2013.01)

(58) Field of Classification Search
CPC ..................... C07D 209/54; C07D 207/16
See application file for complete search history.

(56) References Cited
U.S. PATENT DOCUMENTS
2007/0117986 A1    5/2007    Tanaka et al.

OTHER PUBLICATIONS

Jiang et al., "Highly Enantioselective Synthesis of γ-Nitro Heteroaromatic Ketones in a Doubly Stereocontrolled Manner Catalyzed by Bifunctional Thiourea Catalysts Based on Dehydroabietic Amine: A Doubly Stereocontrolled Approach to Pyrrolidine Carboxylic Acids", Organic Letters, vol. 11, No. 1, 2009, pp. 153-156.
Notice of Reasons for Refusal dated Jul. 21, 2020 in corresponding Japanese Patent Application No. 2019-504149, with English Translation.
International Search Report dated Nov. 29, 2016, in International (PCT) Application No. PCT/JP2016/004377.
Yin et al., "Synthesis of 3-Pyrrolidinecarboxylic Acids via Enantioselective Organocatalytic Michael Addition of Nitroalkanes to 4-Oxopent-2-Enoate Derivatives", The 136 Annual Meeting of the Pharmaceutical Society of Japan, vol. 2, Mar. 5, 2016, p. 148.
Mitchell et al., "A versatile organocatalyst for the asymmetric conjugate addition of nitroalkanes to enones", Chem. Commun., 2005, vol. 42, pp. 5346-5348.
Mitchell et al., "An efficient, asymmetric organocatalyst-mediated conjugate addition of nitroalkanes to unsaturated cyclic and acyclic ketones", Org. Biomol. Chem., 2006, vol. 4, No. 10, pp. 2039-2049.
Juaristi et al., "Asymmetric Synthesis of, β-Amino Acids. 1, Highly Diastereoselective Addition of a Racemic β-Alanine Enolate Derivative to Electrophiles", J. Org. Chem., vol. 56, No. 7, 1991, pp. 2553-2557.
Zhang et al., "Catalysis of 3-Pyrrolidinecarboxylic Acid and Related Pyrrolidine Derivatives in Enantioselective anti-Mannich-Type Reactions: Importance of the 3-Acid Group on Pyrrolidine for Stereocontrol", J. Am. Chem. Soc., vol. 130, No. 3, 2008, pp. 875-886.
Mitsumori et al.," Direct Asymmetric anti-Mannich-Type Reactions Catalyzed by a Designed Amino Acid", J. Am. Chem. Soc., vol. 128, No. 4, 2006, pp. 1040-1041.
Halland et al., "Organocatalytic Asymmetric Conjugate Addition of Nitroalkanes to α, β-Unsaturated Enones Using Novel Imidazoline Catalysts", J. Org. Chem., vol. 67, No. 24, 2002, pp. 8331-8338.
Ballini et al., "Potassium Fluoride/Basic Alumina as Far Superior Heterogeneous Catalyst for the Chemoselective Conjugate Addition of Nitroalkanes to Electron-Poor Alkenes Having Two Electron-Withdrawing Groups in α- and β-Positions", Adv. Synth. Catal., vol. 348, 2006, pp. 1154-1156.
File Registry on STN, RN 1227911-60-5, Jun. 17, 2010, 1 page.
Wang et al., "An efficient enantioselective method for asymmetric Michael addition of nitroalkanes to α, β-unsaturated aldehydes", Chem. Commun., vol. 10, 2008, pp. 1232-1234.
Lu. et al., "Highly enantioselective organocatalytic Michael addition of nitroalkanes to 4-oxo-enoates", Chem. Commun., vol. 28, 2009, pp. 4251-4253.

*Primary Examiner* — Rebecca L Anderson
(74) *Attorney, Agent, or Firm* — Wenderoth, Lind & Ponack, L.L.P.

(57) ABSTRACT

The present invention relates to a process for preparing 3-pyrrolidine carboxylic acid derivatives, and particularly a simple process for preparing 5-substituted 3-pyrrolidine carboxylic acid derivatives. In addition, the present invention relates to a novel pyrrolidine carboxylic acid derivative, its manufacture, pharmaceutical compositions containing it and its use as a catalyst.

2 Claims, No Drawings

CONCISE PROCESS FOR PREPARING 3-PYRROLIDINE CARBOXYLIC ACID DERIVATIVES

TECHNICAL FIELD

The present invention relates to a process for preparing 3-pyrrolidine carboxylic acid derivatives, and particularly a concise process for preparing 5-substituted 3-pyrrolidine carboxylic acid derivatives. In addition, the present invention relates to a novel pyrrolidine carboxylic acid derivative, its manufacture, pharmaceutical compositions and therapeutically active substances containing it and its use as a catalyst.

BACKGROUND ART

Pyrrolidine carboxylic acid derivatives are building blocks found in biologically important compounds. In addition, 3-pyrrolidine carboxylic acid derivatives are catalysts for molecular transforms.

As to pyrrolidine carboxylic acid derivatives, their process for the manufacture in the documents have been known.

CITATION LIST

Patent Literature

[PTL 1] US 2007/0117986 A1

Non Patent Literature

[NPL 1] Mitsumori, S et al, J. Am. Chem. Soc. 2006, 128, 1040

[NPL 2] Zhang, H et al, J. Am. Chem. Soc. 2008, 130, 875

SUMMARY OF INVENTION

Technical Problem

Problems to be solved by the present invention are to provide a novel chemically and biologically important 3-pyrrolidine carboxylic acid derivative and a highly-stereoselective, moderate, atom economic process for preparing 3-pyrrolidine carboxylic acid derivatives.

Solution to Problem

The present inventors have carried out intensive studies, as a result, they have found that by enantioselective Michael reaction with nitroalkanes and carboxylic acid ester substituted derivatives of α,β-unsaturated ketones (or α,β-unsaturated aldehydes) in the presence of amine catalysts, β-carboxylic acid ester substituted enones can be obtained, subsequently by cyclization in the presence of reductants, 3-pyrrolidine carboxylic acid derivatives can be synthesized under highly-stereoselective, moderate, atom economic reaction conditions, whereby the present invention has been accomplished.

Namely, the present invention relates to the following.

(1) A process for preparing compound of formula I:

[Chem.1]

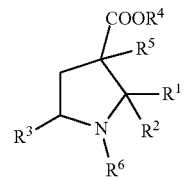

wherein
R$^1$ and R$^2$ are each independently hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl; or
R$^1$ and R$^2$ together form —(CH$_2$)$_n$—, and n is 2 to 6;
R$^3$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl;
R$^4$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl;
R$^5$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl; and
R$^6$ is hydrogen, or amino-protecting group;
or a pharmaceutically acceptable salt thereof, which process comprises
step A: reacting compound of formula II:

[Chem.2]

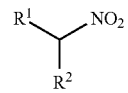

wherein R$^1$ and R$^2$ are as defined above, with compound of formula III:

[Chem.3]

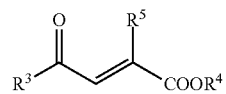

wherein R$^3$, R$^4$ and R$^5$ are as defined above, in the presence of at least one of compound X which is selected from the group of:

[Chem.4]

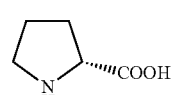

A

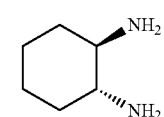

B

-continued

C
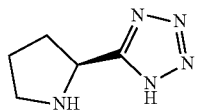

D
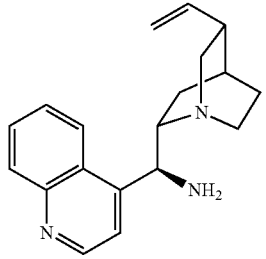

E
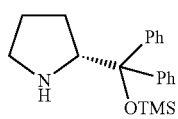

F
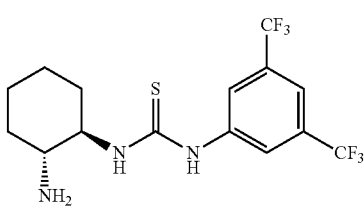

F'
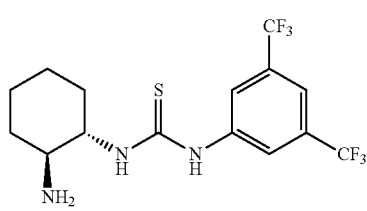

to obtain compound of formula IV:

[Chem. 5]
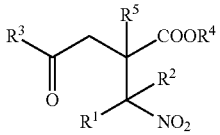

wherein $R^1$, $R^2$, $R^3$, $R^4$, and $R^5$ are as defined above.

(2) A process according to (1) for preparing compound of formula I:

[Chem. 6]
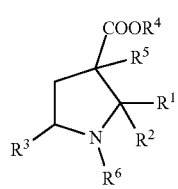

wherein
$R^1$ and $R^2$ are each independently hydrogen, $C_{1-7}$-alkyl, or halo-$C_{1-7}$-alkyl; or
$R^1$ and $R^2$ together form —$(CH_2)_n$—, and n is 2 to 5;

$R^3$ is hydrogen, $C_{1-7}$-alkyl, or halo-$C_{1-7}$-alkyl;

$R^4$ is hydrogen, $C_{1-7}$-alkyl, halo-$C_{1-7}$-alkyl, or aryl-$C_{1-7}$-alkyl;

$R^5$ is hydrogen, $C_{1-7}$-alkyl, or halo-$C_{1-7}$-alkyl; and $R^6$ is hydrogen, or amino-protecting group;

or a pharmaceutically acceptable salt thereof, which process comprises step A: reacting compound of formula II:

[Chem. 7]
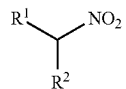

wherein $R^1$ and $R^2$ are as defined above, with compound of formula III:

[Chem. 8]
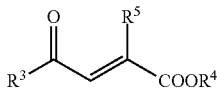

wherein $R^3$, $R^4$ and $R^5$ are as defined above, in the presence of at least one of compound X which is selected from the group of B, D, E, F, and F' to obtain compound of formula IV:

[Chem. 9]
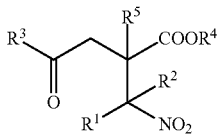

wherein $R^1$, $R^2$, $R^3$, $R^4$, and $R^5$ are as defined above.

(3) A process according to (1) or (2) for preparing compound of formula I:

[Chem.10]
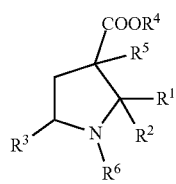

wherein
$R^1$ and $R^2$ are each independently hydrogen or $C_{1-7}$-alkyl; or
$R^1$ and $R^2$ together form —$(CH_2)_n$—, and n is 4 or 5;

$R^3$ is hydrogen or $C_{1-7}$-alkyl;

$R^4$ is hydrogen, $C_{1-7}$-alkyl, or benzyl;

$R^5$ is hydrogen or $C_{1-7}$-alkyl; and $R^6$ is hydrogen, benzoyl, or benzyloxycarbonyl;

or a pharmaceutically acceptable salt thereof, which process comprises step A: reacting compound of formula II:

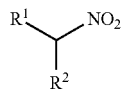
[Chem. 11]

wherein R¹ and R² are as defined above, with compound of formula III:

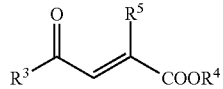
[Chem. 12]

wherein R³, R⁴ and R⁵ are as defined above, in the presence of at least one of compound X which is selected from the group of F and F'
to obtain compound of formula IV:

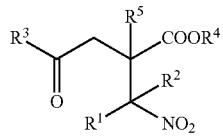
[Chem. 13]

wherein R¹, R², R³, R⁴, and R⁵ are as defined above.

(4) A process according to any one of (1) to (3), which process further comprises reacting the compound of formula II with the compound of formula III, in the presence of an additive.

(5) A process according to (4), wherein
the additive is at least one selected from the group consisting of acetic acid, benzoic acid, and imidazole.

(6) A process according to any one of (1) to (5), which process further comprises
step B: reacting compound of formula IV:

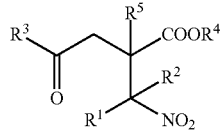
[Chem. 14]

wherein R¹, R², R³, R⁴, and R⁵ are as defined above, with a reductant to obtain compound of formula I':

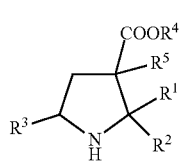
[Chem. 15]

wherein R¹, R², R³, R⁴, and R⁵ are as defined above.

(7) A process according to (6), wherein
the reductant is zinc and acetic acid, or Pd/C and hydrogen.

(8) A process according to any one of (1) to (7), which process further comprises step C: introducing an amino-protecting group into a nitrogen atom of compound of formula I':

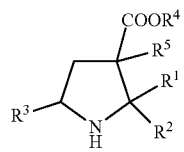
[Chem. 16]

wherein R¹, R², R³, R⁴, and R⁵ are as defined above, to obtain compound of formula I:

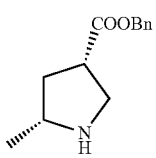
[Chem. 17]

wherein R¹, R², R³, R⁴, R⁵ and R⁶ are as defined above.

(9) Compounds of formula I, I', and IV manufactured by a process according to any one of (1) to (8).

(10) The compound of formula I according to (1) which is selected from the group consisting of:

[Chem. 18]

(3R,5S)-benzyl 5-methylpyrrolidine-3-carboxylate,

[Chem. 19]

(3S,5R)-benzyl 5-methylpyrrolidine-3-carboxylate,

[Chem.20]

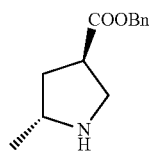

(3R,5R)-benzyl 5-methylpyrrolidine-3-carboxylate,

[Chem.21]

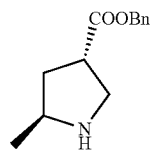

(3S,5S)-benzyl 5-methylpyrrolidine-3-carboxylate,

[Chem.22]

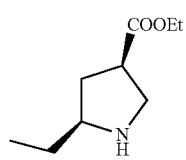

(3R,5S)-ethyl 5-ethylpyrrolidine-3-carboxylate,

[Chem.23]

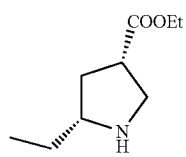

(3S,5R)-ethyl 5-ethylpyrrolidine-3-carboxylate,

[Chem.24]

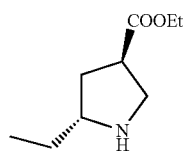

(3R,5R)-ethyl 5-ethylpyrrolidine-3-carboxylate,

[Chem.25]

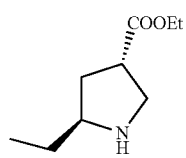

(3S,5S)-ethyl 5-ethylpyrrolidine-3-carboxylate,

[Chem.26]

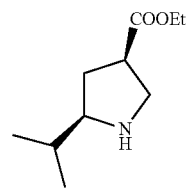

(3R,5S)-ethyl 5-isopropylpyrrolidine-3-carboxylate,

[Chem.27]

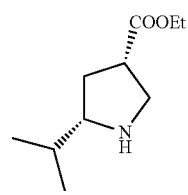

(3S,5R)-ethyl 5-isopropylpyrrolidine-3-carboxylate,

[Chem.28]

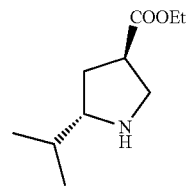

(3R,5R)-ethyl 5-isopropylpyrrolidine-3-carboxylate,

[Chem.29]

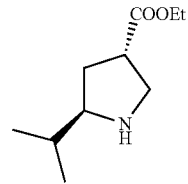

(3S,5S)-ethyl 5-isopropylpyrrolidine-3-carboxylate,

[Chem.30]

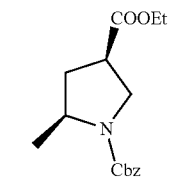

(3R,5S)-1-((benzyloxy)carbonyl)-5-methylpyrrolidine-3-
carboxylic acid ethyl ester,

[Chem.31]

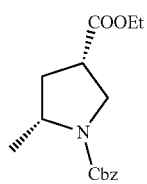

(3S,5R)-1-((benzyloxy)carbonyl)-5-methylpyrrolidine-3-carboxylic acid ethyl ester,

[Chem.32]

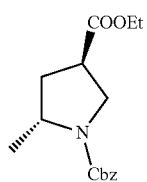

(3R,5R)-1-((benzyloxy)carbonyl)-5-methylpyrrolidine-3-carboxylic acid ethyl ester,

[Chem.33]

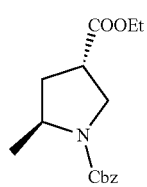

(3S,5S)-1-((benzyloxy)carbonyl)-5-methylpyrrolidine-3-carboxylic acid ethyl ester,

[Chem.34]

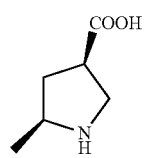

(3R,5S)-5-methylpyrrolidine-3-carboxylic acid,

[Chem. 35]

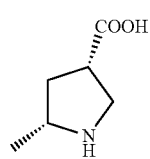

(3S,5R)-5-methylpyrrolidine-3-carboxylic acid,

[Chem. 36]

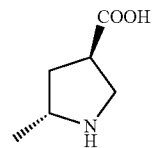

(3R,5R)-5-methylpyrrolidine-3-carboxylic acid

[Chem. 37]

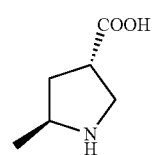

(3S,5S)-5-methylpyrrolidine-3-carboxylic acid

[Chem. 38]

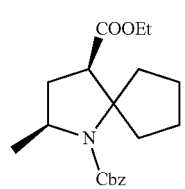

(2S,4R)-1-benzyl 4-ethyl 2-methyl-1-azaspiro[4.4]nonane-1,4-dicarboxylate,

[Chem. 39]

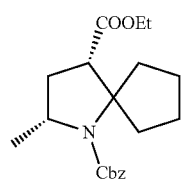

(2R,4S)-1-benzyl 4-ethyl 2-methyl-1-azaspiro[4.4]nonane-1,4-dicarboxylate,

[Chem. 40]

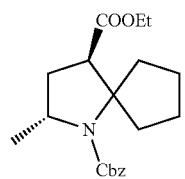

(2R,4R)-1-benzyl 4-ethyl 2-methyl-1-azaspiro[4.4]nonane-1,4-dicarboxylate, and

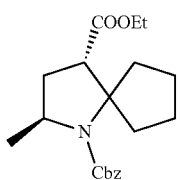

[Chem. 41]

(2S,4S)-1-benzyl 4-ethyl 2-methyl-1-azaspiro[4.4]nonane-1,4-dicarboxylate, or a pharmaceutically acceptable salt thereof.

(11) The compound of formula IV according to (1) which is selected from the group consisting of

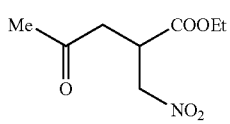

[Chem. 42]

ethyl 2-(nitromethyl)-4-oxopentanoate,

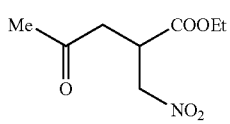

[Chem. 43]

ethyl 2-(2-nitropropan-2-yl)-4-oxopentanoate,

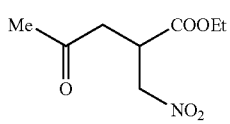

[Chem. 44]

ethyl 2-(1-nitrocyclopentyl)-4-oxopentanoate,

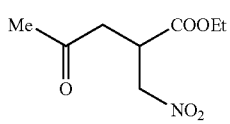

[Chem. 45]

ethyl 2-(1-nitrocyclohexyl)-4-oxopentanoate,

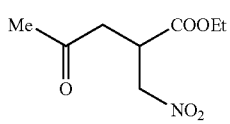

[Chem. 46]

isopropyl 2-(nitromethyl)-4-oxopentanoate,

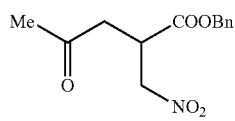

[Chem. 47]

benzyl 2-(nitromethyl)-4-oxopentanoate,

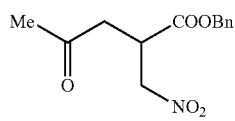

[Chem. 48]

tert-butyl 2-(nitromethyl)-4-oxopentanoate,

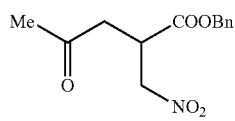

[Chem. 49]

ethyl 2-(nitromethyl)-4-oxohexanoate,

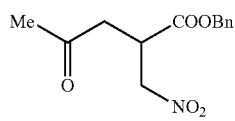

[Chem.50]

benzyl 2-(nitromethyl)-4-oxohexanoate, and

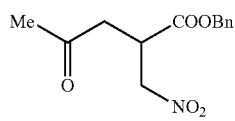

[Chem.51]

ethyl 2-(nitromethyl)-4-oxobutanoate.

(12) A pharmaceutical composition, comprising a compound according to any one of (9) to (11) or a pharmaceutically acceptable salt thereof.

Advantageous Effects of Invention

The present invention can provide a novel, chemically and biologically important, important as catalysts for chemical synthesis, 3-pyrrolidine carboxylic acid derivative and a highly-stereoselective, moderate, atom economic process for preparing 3-pyrrolidine carboxylic acid derivatives.

DESCRIPTION OF EMBODIMENTS

The following provides a detailed explanation of the present invention.

The term "alkyl" refers to a straight-chain or branched-chain alkyl having 1 to 7 carbon atoms, either singly or in combination, preferably a straight-chain or branched-chain alkyl group having 1 to 4 carbon atoms. Examples of straight-chain or branched-chain alkyl groups include methyl, ethyl, propyl, isopropyl, butyl, isobutyl, pentyl, hexyl and heptyl, preferably methyl, ethyl, propyl, isopropyl, butyl, iso-butyl, tert-butyl, or pentyl, more preferably methyl, ethyl, propyl, isopropyl, tert-butyl.

The term "cycloalkyl" refers to a cycloalkyl ring having 3 to 7 carbon atoms, either singly or in combination, preferably a cycloalkyl ring having 3 to 6 carbon atoms. Examples of cycloalkyls include cyclopropyl, cyclobutyl, cyclopentyl, cyclohexyl, cycloheptyl, and cyclooctyl.

The term "alkoxy" denotes a group of the formula: alkyl—O—, wherein the term "alkyl" is as defined above, either singly or in combination, for example, refers to methoxy, ethoxy, n-propoxy, isopropoxy, n-butoxy, sec-butoxy, isobutoxy and tert-butoxy.

The term "halo" refers to halogen, for example fluorine, chlorine, bromine, or iodine, preferably fluorine, chlorine, or bromine, more preferably fluorine, and chlorine, either singly or in combination. The term "halo" means at least one group is replaced with at least one halogen, particularly 1 to 5 halogens, particularly 1 to 4 halogens, namely 1, 2, 3, or 4 halogens, in combination with other groups.

The term "haloalkyl" denotes an alkyl group replaced with at least one halogen, preferably 1 to 5 halogens, more preferably 1 to 3 halogens, either singly or in combination. For example, haloalkyl refers to trifluoro-methyl.

The term "haloalkoxy" or "haloalkyloxy" denotes an alkoxy group replaced with at least one halogen, preferably 1 to 5 halogens, more preferably 1 to 3 halogens, either singly or in combination. For example, haloalkyl refers to trifluoro-methoxy.

The term "aryl" means an aromatic hydrocarbon ring group having 6 to 14 carbon atoms, preferably 6 to 10 carbon atoms, either singly or in combination with other groups, and having at least one aromatic ring or fused ring, at least one of the rings of which is aromatic. Examples of "aryls" include benzyl, biphenyl, indanyl, naphthyl, phenyl (Ph) and the like. Preferably example of "aryl" includes phenyl.

The term "heteroaryl" means an aromatic hydrocarbon ring group having single 4 to 8 membered ring or fused ring having 6 to 14 ring atoms, preferably 6 to 10 ring atoms, either singly or in combination with other groups, and having 1, 2, or 3 hetero atoms selected from N, O, and S, particularly N and O, at least one of the heterocyclic rings of which is aromatic. Examples of "heteroaryls" include benzofuryl, benzimidazolyl, benzoxazinyl, benzothiadiazinyl, benzothiazolyl, benzothienyl, benzo-triazolyl, furyl, imidazolyl, indazolyl, indolyl, isoquinolinyl, isothiazolyl, isoxazolyl, oxazolyl, pyrazinyl, pyrazolyl (pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Preferably examples of heteroaryls include 1H-pyrazolyl, furyl, isoxazolyl, oxazolyl, pyrazinyl, pyrazolyl, pyridazinyl, pyridinyl, pyridinyl-N-oxide, and pyrimidinyl. More preferably examples of heteroaryls include pyridinyl, pyrazolyl, pyrazinyl, and pyrimidinyl. Most preferably examples of heteroaryls include pyridin-2-yl, pyrazin-2-yl, 1H-pyrazol-3-yl, and pyrimidin-2-yl.

The term "protecting group" (PG) means a group blocking selectively a reaction site of a multifunctional compound so that a chemical reaction can selectively occurs at other non-protected reaction site, in a sense related thereto in synthetic chemicals since before. Protecting groups can be removed at the appropriate time. A typical protecting group is amino-protecting group or hydroxyl-protecting group.

Amino-protecting groups include phenylcarbonyl, tert-butoxycarbonyl (Boc), benzyloxycarbonyl (Cbz), fluorenylmethoxycarbonyl (Fmoc), and benzyl (Bn). Amino-protecting groups is preferably Cbz or Bn.

Hydroxyl-protecting groups include methoxymethyl (MOM), 2-methoxyethoxymethyl (MEM), tetrahydropyranyl (THP), trimethylsilyl (TMS), tert-butyldimethylsilyl (TBS or TMDMS), tert-Butyldimethylphenylsilyl (TBDPS), and benzyl (Bn).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Salts may be formed by methods commonly used by a person skilled in the art.

Abbreviation

PhCH$_3$: toluene
CH$_2$Cl$_2$: dichloromethane
EtOAc: ethyl acetate
AcOH: acetic acid
PhCOOH: benzoic acid
Zn: zinc metal
Pd/C: palladium on charcoal or palladium on carbon
P-TSA: p-toluenesulfonic acid
Step A Step A comprises reacting the compound of formula II:

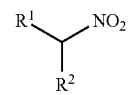

[Chem.52]

wherein
R$^1$ and R$^2$ are each independently hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl; or
R$^1$ and R$^2$ together form —(CH$_2$)$_n$—, and n is 2 to 6;
with the compound of formula III:

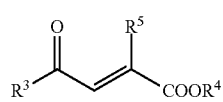

[Chem.53]

wherein $R^3$ is hydrogen, $C_{1-7}$-alkyl, $C_{3-7}$-cycloalkyl, halo-$C_{1-7}$-alkyl, $C_{1-7}$-alkoxy-$C_{1-7}$-alkyl, aryl-$C_{1-7}$-alkyl, or heteroaryl-$C_{1-7}$-alkyl;

$R^4$ is hydrogen, $C_{1-7}$-alkyl, $C_{3-7}$-cycloalkyl, halo-$C_{1-7}$-alkyl, $C_{1-7}$-alkoxy-$C_{1-7}$-alkyl, aryl-$C_{1-7}$-alkyl, or heteroaryl-$C_{1-7}$-alkyl; and $R^5$ is hydrogen, $C_{1-7}$-alkyl, $C_{3-7}$-cycloalkyl, halo-$C_{1-7}$-alkyl, $C_{1-7}$-alkoxy-$C_{1-7}$-alkyl, aryl-$C_{1-7}$-alkyl, or heteroaryl-$C_{1-7}$-alkyl;

in the presence of compound X to obtain the compound of formula IV:

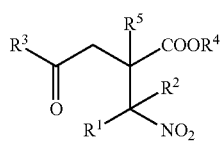
[Chem.54]

wherein $R^1$ to $R^5$ are as defined above.

Step A comprises preferably reacting the compound of formula II:

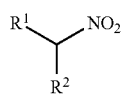
[Chem.55]

wherein $R^1$ and $R^2$ are each independently hydrogen, $C_{1-7}$-alkyl, or halo-$C_{1-7}$-alkyl; or $R^1$ and $R^2$ together form —$(CH_2)_n$—, and n is 2 to 5;

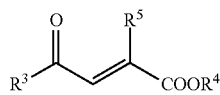
[Chem.56]

wherein $R^3$ is hydrogen, $C_{1-7}$-alkyl, or halo-$C_{1-7}$-alkyl;

$R^4$ is hydrogen, $C_{1-7}$-alkyl, halo-$C_{1-7}$-alkyl, or aryl-$C_{1-7}$-alkyl; and $R^5$ is hydrogen, $C_{1-7}$-alkyl, or halo-$C_{1-7}$-alkyl;

in the presence of compound X to obtain the compound of formula IV:

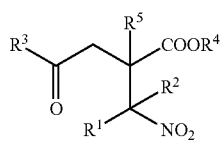
[Chem.57]

wherein $R^1$ to $R^5$ are as defined above.

Step A comprises more preferably reacting the compound of formula II:

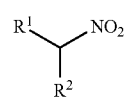
[Chem.58]

wherein $R^1$ and $R^2$ are each independently hydrogen or $C_{1-7}$-alkyl; or $R^1$ and $R^2$ together form —$(CH_2)_n$—, and n is 4 or 5;

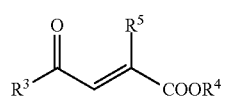
[Chem.59]

wherein $R^3$ is hydrogen or $C_{1-7}$-alkyl;

$R^4$ is hydrogen, $C_{1-7}$-alkyl or benzyl; and $R^5$ is hydrogen or $C_{1-7}$-alkyl;

in the presence of compound X to obtain the compound of formula IV:

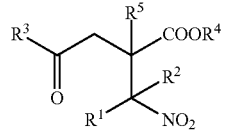
[Chem.60]

wherein $R^1$ to $R^5$ are as defined above.

In step A, the compound of formula II can be used, for example, within the range of 2 to 20 mol equivalents, preferably 3 to 15 mol equivalents, more preferably 4 to 10 mol equivalents, to the compound of formula III.

In step A, the compound of X is, for example, at least one selected from the group of:

[Chem.61]

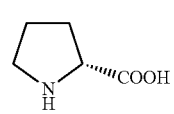
A

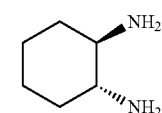
B

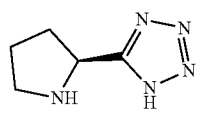
C

-continued

D

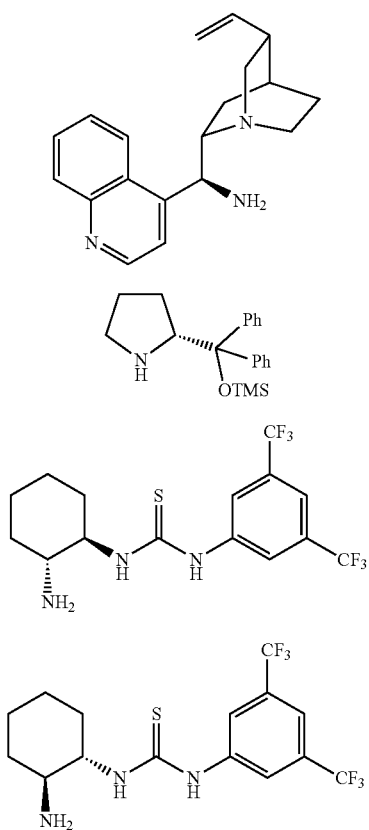

E

F

F'

In step A, the compound of X is preferably, at least one selected from the group of B, D, E, F, and F' described above.

In step A, the compound of X is more preferably, at least one selected from the group of F, and F' described above.

In step A, the compound of X can be used, for example, within the range of 0.05 to 1.0 mol equivalents, preferably 0.1 to 0.5 mol equivalents, more preferably 0.1 to 0.2 mol equivalents, to the compound of formula III.

Step A comprises reacting the compound of formula II with the compound of formula III in the presence of compound X and, optionally an additive, to obtain the compound of formula IV.

In step A, the additive is, for example, at least one selected from the group consisting of carboxylic acid and heterocyclic aromatic amine.

In step A, the additive is, preferably, at least one selected from the group consisting of acetic acid, benzoic acid, and imidazole.

In step A, the additive is, more preferably, at least one selected from the group consisting of acetic acid.

In step A, the additive can be used, for example, within the range of 0.05 to 1.0 mol equivalents, preferably 0.1 to 0.5 mol equivalents, more preferably 0.1 to 0.2 mol equivalents, to the compound of formula III.

In step A, the reaction can be performed in a solvent, the solvent used in step A is not particularly limited unless it is involved in the reaction, and is, for example, $PhCH_3$, o-Xylene, $CH_2Cl_2$, EtOAc and the like, preferably $PhCH_3$, o-Xylene, and $CH_2Cl_2$, more preferably $CH_2Cl_2$.

In step A, the reaction time is not particularly limited when the compound formula III disappears from the reaction mixture, and is, for example, within the range of 2 to 150 hours, preferably 5 to 72 hours, more preferably 5 to 48 hours.

In step A, the reaction temperature is, for example, within the range of −10 to 50° C., preferably 0 to 40° C., more preferably 0 to 25° C.

Step B

Step B comprises reacting the compound of formula IV:

[Chem. 62]

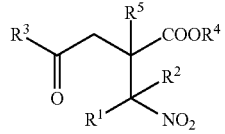

with a reductant, via compound of formula IV':

[Chem. 63]

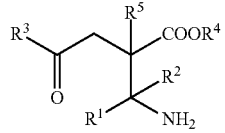

to obtain compound of formula I':

[Chem. 64]

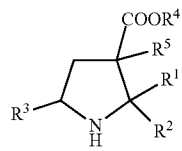

wherein $R^1$ to $R^5$ are as defined above.

In step B, the reductants include zinc and acetic acid, or Pd/C (Pd on charcoal) and hydrogen ($H_2$ gas) optionally in the presence of acid such as P-TSA, for example.

In step B, the reductant is used with the compound formula IV, as necessary.

In step B, the reaction can be performed in a solvent, the solvent used in step B is not particularly limited unless it is involved in the reaction, and is, for example, MeOH and the like.

In step B, the reaction time is not limited when the compound formula IV disappears from the reaction mixture, and is, for example, within the range of 1 to 72 hours.

In step B, the reaction temperature is, for example, within the range of 10 to 30° C.

Step C

Step C comprises introducing an amino-protecting group into the nitrogen atom of the compound of formula I':

[Chem. 65]

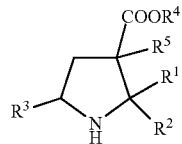

by a common method in the art (see, for example, Greene's Protective Groups in Organic Synthesis 4th edition, Wiley-Interscience, 2006), to obtain the compound of formula I:

[Chem.66]

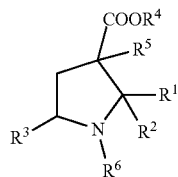

wherein
$R^1$ to $R^5$ are as defined above,
$R^6$ is, for example, hydrogen, or amino-protecting group; $R^6$ is preferably hydrogen, benzoyl, or benzyloxycarbonyl;

One aspect of the invention is a compound of formula I, I', IV, or IV' for use as therapeutically active substances.

Pharmaceutical Compositions

One aspect of the invention is a pharmaceutical composition, comprising the compound of formula I, I', IV, or IV' or the pharmaceutically acceptable salt thereof, and a pharmaceutically acceptable adjuvant.

The compound of formula I, I', IV, or IV', as well as the pharmaceutically acceptable salt thereof is used as medicaments, for example, in the form of pharmaceutical preparations. The pharmaceutical preparations can be administered orally, for example, in the form of tablets, coated tablets, dragees, hard and soft capsules, solutions, emulsions or suspensions. The administration can, however, also be effected rectally, for example, in the form of suppositories, or parenterally, for example, in the form of injection solutions.

The compound of formula I, I', IV, or IV' and the pharmaceutically acceptable salt thereof can be processed with pharmaceutically inert, inorganic or organic excipients for the production of tablets, coated tablets, dragees, hard gelatine capsules. Lactose, corn starch or derivatives thereof, talc, stearic acids or its salts and the like can be used, for example, as such excipients for tablets, dragees and hard gelatine capsules.

Suitable excipients for soft gelatine capsules are, for example, vegetable oils, waxes, fats, semi-solid and liquid polyols and the like.

Suitable excipients for the production of solutions and syrups are, for example, water, polyols, sucrose, invert sugars, glucose and the like.

Suitable excipients for injection solutions are, for example, water, alcohols, polyols, glycerol, vegetable oils and the like.

Suitable excipients for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, have to be adjusted to the individual requirements in each particular case. Generally, in the case of oral administration, the dosage per day from about 10 to 1000 mg of the compound of formula I or II is appropriate for one person, the upper limit above can also be exceeded when this is found to be needed.

EXAMPLES

The present invention will be described below in more detail by showing Examples, but the present invention is not intended to be limited by these Examples.

Example 1

The conditions shown below were tested, and the catalysts were screened.

TABLE 1

Screening of Catalyst Systems and Conditions[a]

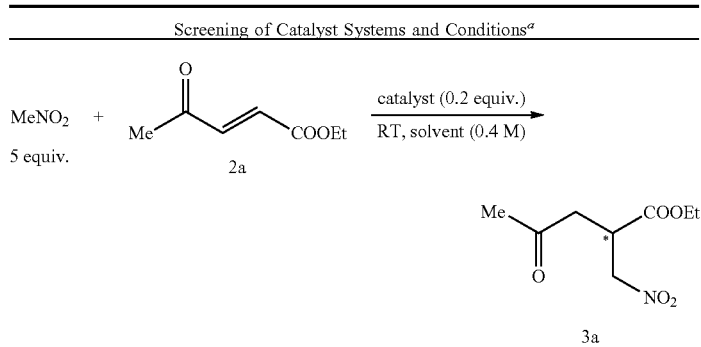

| entry | catalyst | solvent | additive (0.2 equiv.) | time (h) | temperature (° C.) | yield (%) | ee (%) |
|---|---|---|---|---|---|---|---|
| 1 | A | PhCH$_3$ | — | 48 | RT | 0 | — |
| 2 | B | PhCH$_3$ | — | 48 | RT | 10 | −20 |
| 3 | C | PhCH$_3$ | — | 48 | RT | 0 | — |
| 4 | D | PhCH$_3$ | — | 48 | RT | 14 | 21 |
| 5 | E | PhCH$_3$ | — | 48 | RT | 7 | N.D. |
| 6 | F | PhCH$_3$ | — | 48 | RT | 51 | 82 |
| 7 | F | o-Xylene | — | 48 | RT | 58 | 89 |

TABLE 1-continued

Screening of Catalyst Systems and Conditions[a]

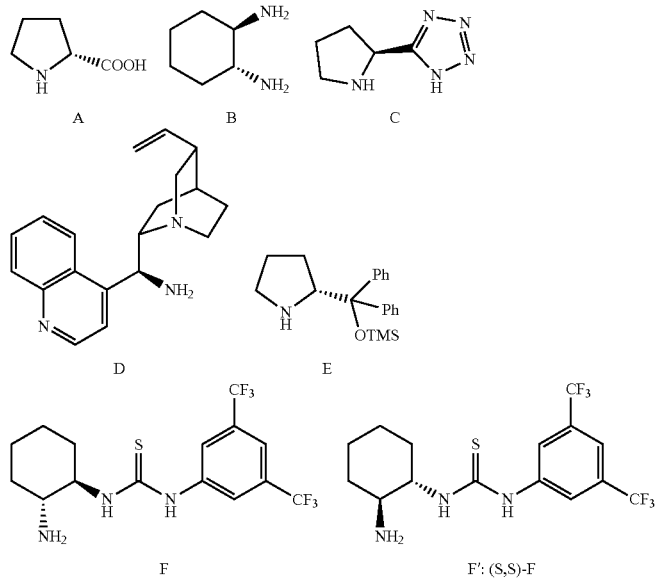

| entry | catalyst | solvent | additive (0.2 equiv.) | time (h) | temperature (°C.) | yield (%) | ee (%) |
|---|---|---|---|---|---|---|---|
| 8  | F  | CH$_2$Cl$_2$ | —         | 48  | RT | 70 | 91 |
| 9  | F  | EtOAc        | —         | 48  | RT | 42 | N.D. |
| 10 | F  | CH$_2$Cl$_2$ | AcOH      | 48  | RT | 50 | 89 |
| 11 | F  | CH$_2$Cl$_2$ | PhCOOH    | 48  | RT | 52 | 90 |
| 12 | F  | CH$_2$Cl$_2$ | Imidazole | 48  | RT | 59 | N.D. |
| 13 | F  | CH$_2$Cl$_2$ | —         | 48  | 0  | 42 | 92 |
| 14 | F  | CH$_2$Cl$_2$ | AcOH      | 48  | 0  | 37 | 96 |
| 15 | F  | CH$_2$Cl$_2$ | AcOH      | 120 | 10 | 76 | 94 |
| 16 | F' | CH$_2$Cl$_2$ | AcOH      | 120 | 10 | 83 | −94 |

[a]Reaction conditions: Enone 2a (0.2 mmol, 1.0 equiv), nitromethane (1.0 mmol, 5.0 equiv), catalyst (0.04 mmol, 0.2 equiv), and additive (if added, 0.04 mmol, 0.2 equiv) in solvent (0.2 mL). RT = 24° C.
N.D. = not determined.

Procedure for the Screening of Catalyst Systems (Table 1).

To a solution of catalyst (0.04 mmol) in solvent (0.2 mL) were added additive (if used, 0.04 mmol), enone 2a (0.2 mmol) and nitromethane (1.0 mmol) at room temperature (24° C.). The mixture (initially suspension) was stirred at the same temperature and the progress of the reaction was monitored by TLC. At the indicated time point in the table, the mixture was poured into 1 M HCl solution (1.0 mL) and extracted with CH$_2$Cl$_2$. Organic layers were combined, washed with brine, dried over Na$_2$SO$_4$, concentrated, and purified by flash column chromatography (hexane/EtOAc=4:1) to afford 3a. The dr was determined by $^1$H NMR analysis before purification, the ee was determined by chiral-phase HPLC.

Racemic standards of Michael Addition product 3a were prepared by the reaction between enone 2a and nitromethane with (±)-amine catalyst F as catalyst, by the similar procedure used for the reactions.

<Entry 8>

Ethyl 4-oxopentanoate (28.4 mg, 0.20 mmol) was dissolved in CH$_2$Cl$_2$ 0.2 mL, and then nitromethane (54 μL, 1.0 mmol) and catalyst F (15.4 mg, 0.04 mmol) were added, and followed by stirring at room temperature for 48 hours. The reaction mixture was poured into 1N HCl solution, and extracted with CH$_2$Cl$_2$. Organic layers was combined, washed with saturated saline, dried over Na$_2$SO$_4$, and then concentrated under reduced pressure, purified with a silica gel flash column (hexane: ethyl acetate=4:1), to give target conjugate addition product (48.2 mg, 70%). Other entries were also carried out according to Entry 8 method.

Example 2

Using the conditions shown below, the compound 3 in the following Table 2 was synthesized according to Entry 8 method of Example 1.

TABLE 2

Various Nitro Alkanes

| entry | $R^1$ | $R^2$ | temperature (°C.) | time (h) | yield (%) | ee (%) |
|---|---|---|---|---|---|---|
| 1 | H | H | 0 | 120 | 76 | 94 |
| 2 | Me | H | 25 | 24 | 99 | N.D. |
| 3 | Me | Me | 45 | 24 | 90 | 92 |
| 4 | $R^1 = R^2 = (CH_2)_4$ | | 45 | 48 | 65 | 92 |
| 5 | $R^1 = R^2 = (CH_2)_3$ | | 25 | 24 | 85 | 93 |

Example 3

Using the conditions shown below, the compound 3 in the following Table 3 was synthesized according to Entry 8 method of Example 1.

TABLE 3

Various Ester Groups

| entry | Additive (0.2 equiv.) | $R^4$ | yield (%) | ee (%) |
|---|---|---|---|---|
| 7 | AcOH | i-Pr | 75 | 94 |
| 8 | — | Bn | 72 | 92 |
| 9 | — | t-Bu | 79 | 93 |

Example 4

TABLE 4

Michael Addition Reactions[a]

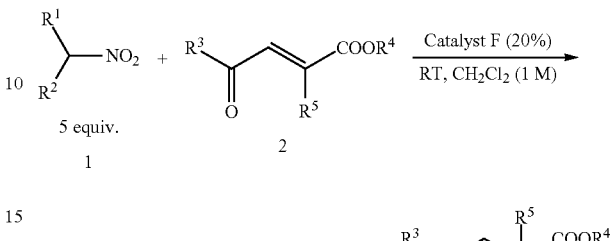

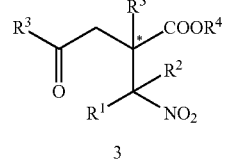

3a, yield 76%, ee 94%[b,f]

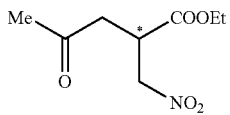

3a, yield 70%, ee 94%[b,d,f]

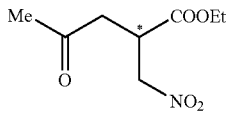

3b, yield 99%, d.r. = 1:1, ee 90% and 93%

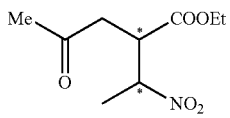

3c, yield 90%, ee 97%[c]

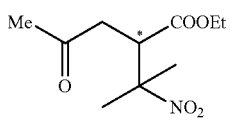

3d, yield 65%, ee 92%[e]

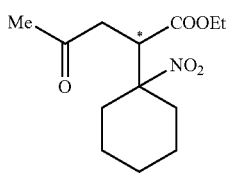

3e, yield 85%, ee 93%

TABLE 4-continued

Michael Addition Reactions[a]

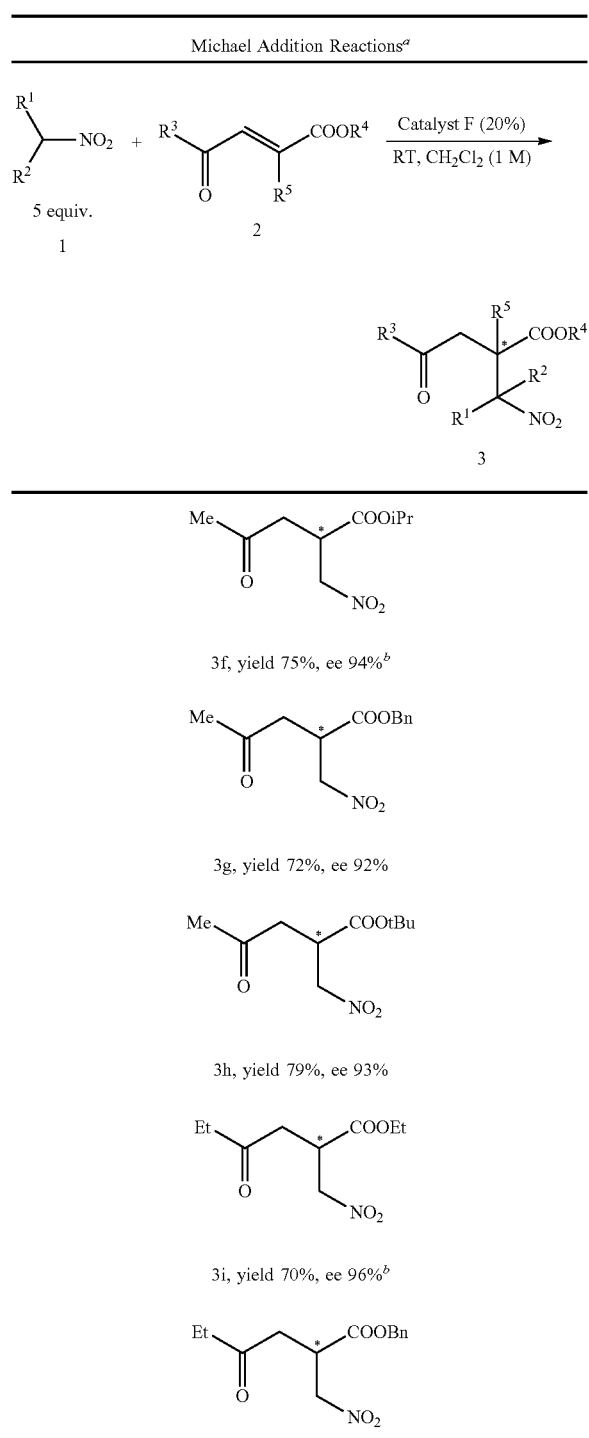

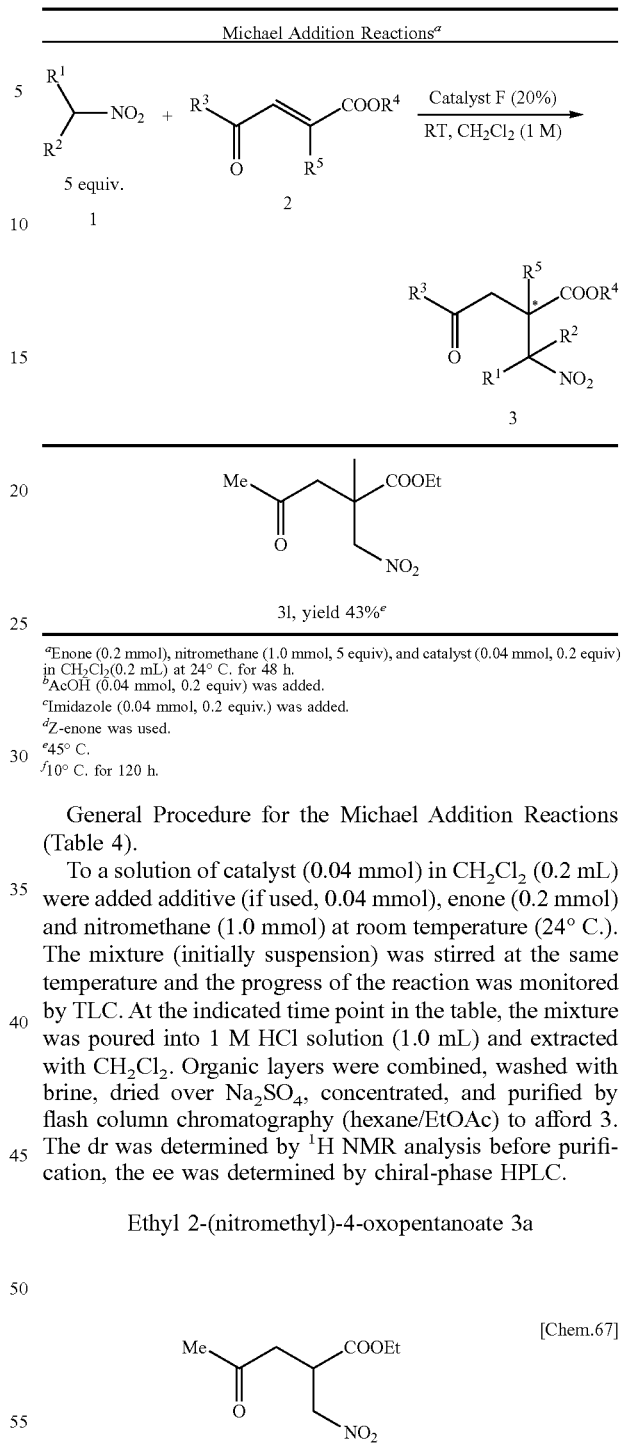

[a]Enone (0.2 mmol), nitromethane (1.0 mmol, 5 equiv), and catalyst (0.04 mmol, 0.2 equiv) in $CH_2Cl_2$ (0.2 mL) at 24° C. for 48 h.
[b]AcOH (0.04 mmol, 0.2 equiv) was added.
[c]Imidazole (0.04 mmol, 0.2 equiv.) was added.
[d]Z-enone was used.
[e]45° C.
[f]10° C. for 120 h.

General Procedure for the Michael Addition Reactions (Table 4).

To a solution of catalyst (0.04 mmol) in $CH_2Cl_2$ (0.2 mL) were added additive (if used, 0.04 mmol), enone (0.2 mmol) and nitromethane (1.0 mmol) at room temperature (24° C.). The mixture (initially suspension) was stirred at the same temperature and the progress of the reaction was monitored by TLC. At the indicated time point in the table, the mixture was poured into 1 M HCl solution (1.0 mL) and extracted with $CH_2Cl_2$. Organic layers were combined, washed with brine, dried over $Na_2SO_4$, concentrated, and purified by flash column chromatography (hexane/EtOAc) to afford 3. The dr was determined by $^1H$ NMR analysis before purification, the ee was determined by chiral-phase HPLC.

Ethyl 2-(nitromethyl)-4-oxopentanoate 3a

<Procedure>
To a solution of catalyst F (15.4 mg, 0.04 mmol) in $CH_2Cl_2$ (0.2 mL) were added acetic acid (1.8 μL, 0.04 mmol), ethyl 4-oxopent-2-enoate (28.4 mg, 0.2 mmol) and nitromethane (54.2 μL, 1.0 mmol) at 10° C. The mixture (initially suspension) was stirred at the same temperature and the progress of the reaction was monitored by TLC. After 120 h (5 days), the mixture was poured into 1 M HCl solution (1.0 mL) and extracted with CH2Cl2. Organic layers were combined, dried over $Na_2SO_4$, concentrated, and purified by flash column chromatography (hexane/EtOAc=4:1) to afford product 3a (30.9 mg, 76%, 94% ee).

<Large Scale>

To a solution of catalyst F (819.5 mg) in CH$_2$Cl$_2$ (10.0 mL) were added ethyl 4-oxopent-2-enoate (2.14 g, 15.0 mmol) and nitromethane (4.0 mL) at room temperature (24° C.). The mixture (initially suspension) was stirred at the same temperature and the progress of the reaction was monitored by TLC. After 4 days, the mixture was poured into 1 M HCl solution (15 mL) and extracted with CH$_2$Cl$_2$. Organic layers were combined, dried over Na$_2$SO$_4$, concentrated, and purified by flash column chromatography (hexane/EtOAc=4:1) to afford product 3a (2.1 g, 69%).

<Chemical Data>

Pale yellow oil. $^1$H NMR (400 MHz, CDCl$_3$): δ 4.77-4.66 (m, 2H), 4.23-4.15 (m, 2H), 3.57-3.49 (m, 1H), 3.04 (dd, J=18.6 Hz, 5.6 Hz, 1H), 2.81 (dd, J=18.6 Hz, 6.6 Hz, 1H), 2.20 (s, 3H), 1.25 (t, J=7.1 Hz, 3H). $^{13}$C NMR (100 MHz, CDCl$_3$): δ 204.9, 170.5, 61.9, 41.4, 28.2, 29.9, 13.9. ESI-HRMS: calcd for C$_8$H$_{14}$O$_5$N ([M+H]$^+$)204.0872, found 204.0849. HPLC (Daicel Chiralpak IA, hexane/i-PrOH=95/5, flow rate 0.5 mL/min, λ=220 nm): t$_R$(major enantiomer) =27.0 min, t$_R$ (minor enantiomer)=24.4 min.

Ethyl 2-(1-nitroethyl)-4-oxopentanoate 3b

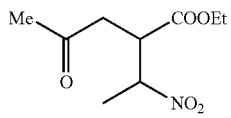

[Chem.68]

<Procedure>

Synthesized according to preparation of compound 3a, by using nitroethane instead of nitromethane, without addition of acetic acid at room temperature (24° C.) for 48 h.

<Chemical Data>

Pale yellow oil. $^1$H NMR (400 MHz, CDCl$_3$): δ 5.01-4.90 (m, 2H), 4.26-4.13 (m, 2H), 3.48-3.39 (m, 1H), 3.05 (dd, J=17.9 Hz, 9.4 Hz, 1H), 2.53 (dd, J=17.9 Hz, 3.6 Hz, 1H), 2.21 (s, 3H), 1.57 (d, J=6.9 Hz, 3H), 1.27 (t, J=7.2 Hz, 3H). $^{13}$C NMR (100 MHz, CDCl$_3$): δ 204.9, 170.6, 82.5, 61.8, 44.2, 40.5, 29.9, 16.8, 14.0. ESI-HRMS: calcd for C$_9$H$_{16}$O$_5$N ([M+H]$^+$) 218.1028, found 218.1004. HPLC (Daicel Chiralpak AS, hexane/i-PrOH=95/5, flow rate 0.5 mL/min, λ=220 nm): t$_R$(major enantiomer)=38.4 min, t$_R$ (minor enantiomer)=44.8 min.

The other diastereomer:

Pale yellow oil. $^1$H NMR (400 MHz, CDCl$_3$): δ 4.99-4.88 (m, 2H), 4.18 (q, J=7.2 Hz, 2H), 3.67-3.59 (m, 1H), 3.01 (dd, J=18.1 Hz, 8.5 Hz, 1H), 2.67 (dd, J=18.0 Hz, 4.4 Hz, 1H), 2.21 (s, 3H), 1.55 (d, J=6.8 Hz, 3H), 1.26 (t, J=7.2 Hz, 3H). $^{13}$C NMR (100 MHz, CDCl$_3$): δ 204.8, 170.5, 82.0, 61.8, 43.6, 40.3, 30.0, 16.2, 14.0. ESI-HRMS: calcd for C$_9$H$_{16}$O$_5$N ([M+H]$^+$) 218.1028, found 218.1004. HPLC (Daicel Chiralpak AS, hexane/i-PrOH=75/25, flow rate 0.5 mL/min, λ=220 nm): t$_R$ (major enantiomer)=14.1 min, t$_R$ (minor enantiomer)=13.6 min.

Ethyl 2-(2-nitropropan-2-yl)-4-oxopentanoate 3c

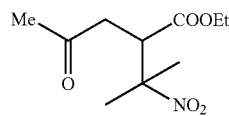

[Chem.69]

<Procedure>

Synthesized according to preparation of compound 3a, by using 2-nitropropane instead of nitromethane, and by using imidazole instead of acetic acid, at room temperature (24° C.) for 48 h.

<Chemical Data>

Pale yellow oil. $^1$H NMR (400 MHz, CDCl$_3$): δ 4.17 (q, J=7.1 Hz, 2H), 3.66 (dd, J=11.2 Hz, 2.4 Hz, 1H), 3.04 (dd, J=17.8 Hz, 11.2 Hz, 1H), 2.41 (dd, J=17.8 Hz, 2.4 Hz, 1H), 2.17 (s, 3H), 1.63 (s, 3H), 1.59 (s, 3H), 1.27 (t, J=7.1 Hz, 3H). $^{13}$C NMR (100 MHz, CDCl$_3$): δ 204.9, 170.8, 88.3, 61.6, 48.3, 41.4, 29.8, 25.5, 23.1, 14.0. ESI-HRMS: calcd for C$_{10}$H$_{18}$O$_5$N ([M+H]$^+$) 232.1179, found 232.1173. HPLC (Daicel Chiralpak AS, hexane/i-PrOH=97/3, flow rate 0.5 mL/min, λ=220 nm): t$_R$ (major enantiomer)=27.7 min, t$_R$ (minor enantiomer)=25.7 min.

Ethyl 2-(1-nitrocyclopentyl)-4-oxopentanoate 3e

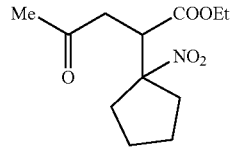

[Chem.70]

<Procedure>

To a solution of catalyst F (15.4 mg, 0.04 mmol) in CH$_2$Cl$_2$ (0.2 mL) were added ethyl 4-oxopent-2-enoate (28.4 mg, 0.2 mmol) and nitrocyclopentane (106.0 μL, 1.0 mmol) at room temperature (24° C.). The mixture (initially suspension) was stirred at the same temperature and the progress of the reaction was monitored by TLC. After 48 h (2 days), the mixture was poured into 1 M HCl solution (1.0 mL) and extracted with CH$_2$Cl$_2$. Organic layers were combined, dried over Na$_2$SO$_4$, concentrated, and purified by flash column chromatography (hexane/EtOAc=4:1) to afford product 3e (43.7 mg, 85%, 93% ee).

<Chemical Data>

Pale yellow oil. $^1$H NMR (400 MHz, CDCl$_3$): δ 4.21-4.12 (m, 2H), 3.56 (dd, J=10.8 Hz, 2.9 Hz, 1H), 3.07 (dd, J=18.0 Hz, 10.8 Hz, 1H), 2.70-2.60 (m, 1H), 2.58-2.46 (m, 2H), 2.17 (s, 3H), 2.12-2.00 (m, 1H), 1.96-1.84 (m, 1H), 1.80-1.64 (m, 4H), 1.26 (t, J=7.1 Hz, 3H). $^{13}$C NMR (100 MHz, CDCl$_3$): δ 205.3, 170.7, 100.3, 61.5, 47.3, 42.1, 36.8, 35.3, 29.8, 24.0, 23.6, 14.0. ESI-HRMS: calcd for C$_{12}$H$_{20}$O$_5$N ([M+H]$^+$) 258.1341, found 258.1319. HPLC (Daicel Chiralpak AS, hexane/i-PrOH=98/2, flow rate 0.5 mL/min, λ=220 nm): t$_R$(major enantiomer)=28.4 min, t$_R$ (minor enantiomer)=27.2 min.

Ethyl 2-(1-nitrocyclohexyl)-4-oxopentanoate 3d

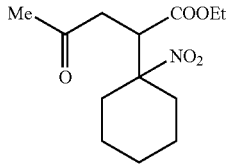

<Procedure>
Synthesized according to preparation of compound 3e, by using nitrocyclohexane instead of nitrocyclopentane, at 45° C.

<Chemical Data>
Pale yellow oil. $^1$H NMR (400 MHz, CDCl$_3$): δ 4.17 (q, J=7.1 Hz, 2H), 3.30 (dd, J=11.4 Hz, 3.0 Hz, 1H), 3.04 (dd, J=18.0 Hz, 11.4 Hz, 1H), 2.57-2.42 (m, 3H), 2.15 (s, 3H), 1.77-1.52 (m, 4H), 1.46-1.12 (m, 7H). $^{13}$C NMR (100 MHz, CDCl$_3$): δ 205.3, 170.6, 91.8, 61.5, 49.2, 40.9, 33.3, 31.4, 29.9, 24.4, 22.2, 22.1, 14.0. ESI-HRMS: calcd for C$_{13}$H$_{22}$O$_5$N ([M+H]$^+$) 272.1498, found 272.1470. HPLC (Daicel Chiralpak IA, hexane/i-PrOH=95/5, flow rate 0.5 mL/min, λ=220 nm): t$_R$ (major enantiomer)=20.1 min, t$_R$ (minor enantiomer)=17.9 min.

Isopropyl 2-(nitromethyl)-4-oxopentanoate 3f

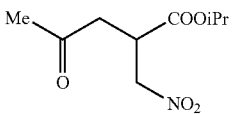

<Procedure>
Synthesized according to preparation of compound 3a, by using isopropyl 4-oxopent-2-enoate instead of ethyl 4-oxopent-2-enoate, at room temperature (24° C.) for 48 h.

<Chemical Data>
Pale yellow oil. $^1$H NMR (400 MHz, CDCl$_3$): δ 5.11-4.99 (m, 1H), 4.71 (ddd, J=20.1 Hz, 14.2 Hz, 5.8 Hz, 1H), 3.54-3.46 (m, 1H), 3.03 (dd, J=18.5 Hz, 5.6 Hz, 1H), 2.80 (dd, J=18.5 Hz, 6.6 Hz, 1H), 2.21 (s, 3H), 1.24 (d, J=6.2 Hz, 6H). $^{13}$C NMR (100 MHz, CDCl$_3$): δ 204.9, 170.0, 69.7, 41.4, 38.4, 29.9, 21.6, 21.5. ESI-HRMS: calcd for C$_9$H$_{16}$O$_5$N ([M+H]$^+$) 218.1028, found 218.1004. HPLC (Daicel Chiralpak AS, hexane/i-PrOH=95/5, flow rate 0.5 mL/min, λ=220 nm): t$_R$ (major enantiomer)=45.1 min, t$_R$ (minor enantiomer)=43.2 min.

Benzyl 2-(nitromethyl)-4-oxopentanoate 3g

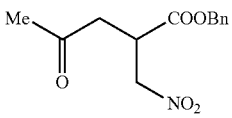

<Procedure>
Synthesized according to preparation of compound 3a, by using benzyl 4-oxopent-2-enoate instead of ethyl 4-oxopent-2-enoate, without addition of acetic acid at room temperature (24° C.) for 48 h.

<Chemical Data>
Pale yellow oil. $^1$H NMR (400 MHz, CDCl$_3$): δ 7.73-7.28 (m, 5H), 5.16 (s, 2H), 4.80-4.67 (m, 2H), 3.64-3.55 (m, 1H), 3.03 (dd, J=18.6 Hz, 5.5 Hz, 1H), 2.82 (dd, J=18.6 Hz, 6.5 Hz, 1H), 2.17 (s, 3H). $^{13}$C NMR (100 MHz, CDCl$_3$): δ 204.8, 170.4, 135.0, 128.7, 128.6, 128.3, 74.6, 67.6, 41.4, 38.3, 29.8. ESI-HRMS: calcd for C$_{13}$H$_{16}$O$_5$N ([M+H]$^+$) 266.1028, found 266.1003. HPLC (Daicel Chiralpak AS, hexane/i-PrOH=95/5, flow rate 0.5 mL/min, λ=220 nm): t$_R$ (major enantiomer)=44.8 min, t$_R$ (minor enantiomer)=39.0 min.

tert-Butyl 2-(nitromethyl)-4-oxopentanoate 3h

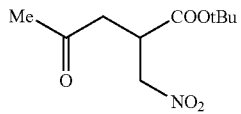

<Procedure>
Synthesized according to preparation of compound 3a, by using tert-butyl 4-oxopent-2-enoate instead of ethyl 4-oxopent-2-enoate, without addition of acetic acid at room temperature (24° C.) for 48 h.

<Chemical Data>
Pale yellow oil. $^1$H NMR (400 MHz, CDCl$_3$): δ 4.73-4.61 (m, 2H), 3.49-3.41 (m, 1H), 2.99 (dd, J=18.5 Hz, 5.7 Hz, 1H), 2.76 (dd, J=18.5 Hz, 6.6 Hz, 1H), 2.20 (s, 3H), 1.44 (s, 9H). $^{13}$C NMR (100 MHz, CDCl$_3$): δ 205.2, 169.5, 82.6, 74.9, 41.5, 39.0, 29.9, 27.8. ESI-HRMS: calcd for C$_{10}$H$_{18}$O$_5$N ([M+H]$^+$) 232.1179, found 232.1173. HPLC (Daicel Chiralpak IA, hexane/i-PrOH=99/1, flow rate 0.5 mL/min, λ=220 nm): t$_R$ (major enantiomer)=34.3 min, t$_R$ (minor enantiomer)=32.3 min.

Ethyl 2-(nitromethyl)-4-oxohexanoate 3i

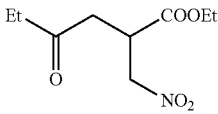

<Procedure>
Synthesized according to preparation of compound 3a, by using ethyl 4-oxohex-2-enoate instead of ethyl 4-oxopent-2-enoate, at room temperature (24° C.) for 48 h.

<Chemical Data>
Pale yellow oil. $^1$H NMR (400 MHz, CDCl$_3$): δ 4.78-4.67 (m, 2H), 4.25-4.15 (m, 2H), 3.60-3.51 (m, 1H), 3.00 (dd, J=18.3 Hz, 5.6 Hz, 1H), 2.77 (dd, J=18.3 Hz, 6.5 Hz, 1H), 2.57-2.42 (m, 2H), 1.26 (t, J=7.1 Hz, 3H), 1.08 (t, J=7.3 Hz, 3H). $^{13}$C NMR (100 MHz, CDCl$_3$): δ 207.9, 170.6, 74.8, 61.8, 40.1, 38.2, 36.0, 14.0, 7.6. ESI-HRMS: calcd for C$_9$H$_{16}$O$_5$N ([M+H]$^+$) 218.1028, found 218.1004. HPLC (Daicel Chiralpak AS, hexane/i-PrOH=95/5, flow rate 0.5

Benzyl 2-(nitromethyl)-4-oxohexanoate 3j

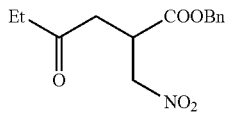
[Chem.76]

<Procedure>

Synthesized according to preparation of compound 3a, by using benzyl 4-oxohex-2-enoate instead of ethyl 4-oxopent-2-enoate, at room temperature (24° C.) for 48 h.

<Chemical Data>

Pale yellow oil. $^1$H NMR (400 MHz, CDCl$_3$): δ 7.45-7.28 (m, 5H), 5.16 (s, 2H), 4.82-4.68 (m, 2H), 3.67-3.57 (m, 1H), 3.00 (dd, J=18.3 Hz, 5.6 Hz, 1H), 2.78 (dd, J=18.3 Hz, 6.5 Hz, 1H), 2.51-2.36 (m, 2H), 1.05 (t, J=7.3 Hz, 3H). $^{13}$C NMR (100 MHz, CDCl$_3$): δ 207.8, 170.5, 135.0, 128.7, 128.6, 128.3, 74.7, 67.6, 40.1, 38.2, 36.0, 7.6. ESI-HRMS: calcd for C$_{14}$H$_{18}$O$_5$N ([M+H]$^+$) 280.1179, found 280.1173. HPLC (Daicel Chiralpak AS, hexane/i-PrOH=95/5, flow rate 0.5 mL/min, λ=220 nm): t$_R$ (major enantiomer)=56.7 min, t$_R$ (minor enantiomer)=48.8 min.

Ethyl 2-(nitromethyl)-4-oxobutanoate 3k

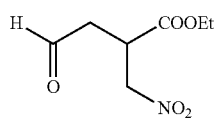 [SMILES: CCOC(=O)C(CC=O)C[N+](=O)[O-]]
[Chem.77]

<Procedure>

To a solution of catalyst F (15.4 mg, 0.04 mmol) in CH$_2$Cl$_2$ (0.2 mL) were added ethyl (E)-4-oxobut-2-enoate (25.6 mg, 0.2 mmol) and nitromethane (54.2 μL, 1.0 mmol) at room temperature (24° C.). The mixture (initially suspension) was stirred at the same temperature and the progress of the reaction was monitored by TLC. After 48 h (2 days), the mixture was poured into 1 M HCl solution (1.0 mL) and extracted with CH$_2$Cl$_2$. Organic layers were combined, dried over Na2SO4, concentrated, and purified by flash column chromatography (hexane/EtOAc=4:1) to afford product 3k (17.8 mg, 47%).

<Chemical Data>

Pale yellow oil. $^1$H NMR (400 MHz, CDCl$_3$): δ 9.78 (s, 1H), 4.77 (dd, J=14.4 Hz, 6.1 Hz, 1H), 4.69 (dd, J=14.4 Hz, 6.1 Hz, 1H), 4.22 (q, J=7.1 Hz, 2H), 3.64-3.56 (m, 1H), 3.10 (dd, J=19.1 Hz, 5.7 Hz, 1H), 2.88 (dd, J=19.1 Hz, 5.7 Hz, 1H), 1.27 (t, J=7.1 Hz, 3H). $^{13}$C NMR (100 MHz, CDCl$_3$): δ 197.9, 170.1, 74.4, 62.1, 42.0, 37.0, 14.0. ESI-HRMS: calcd for C$_7$H$_{12}$O$_5$N ([M+H]$^+$) 190.0710, found 190.0704.

Ethyl 2-methyl-2-(nitromethyl)-4-oxopentanoate 31

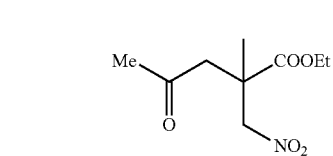
[Chem.78]

<Procedure>

To a solution of catalyst F (15.4 mg, 0.04 mmol) in toluene (0.2 mL) were added ethyl (E)-2-methyl-4-oxopent-2-enoate (0.2 mmol, 31.2 mg) and nitromethane (54.2 μL, 1.0 mmol) at room temperature (24° C.). The mixture (initially suspension) was stirred at 45° C. and the progress of the reaction was monitored by TLC. After 48 h (2 days), the mixture was poured into 1 M HCl solution (1.0 mL) and extracted with CH$_2$Cl$_2$. Organic layers were combined, dried over Na$_2$SO$_4$, concentrated, and purified by flash column chromatography (hexane/EtOAc=4:1) to afford product 31 (18.7 mg, 43%).

<Chemical Data>

Pale yellow oil. $^1$H NMR (400 MHz, CDCl$_3$): δ 4.90 (d, J=12.0 Hz, 1H), 4.80 (d, J=12.0 Hz, 1H), 4.25-4.15 (m, 2H), 3.04 (d, J=18.6 Hz, 1H), 2.90 (d, J=18.6 Hz, 1H), 2.17 (s, 3H), 1.36 (s, 3H), 1.26 (t, J=7.1 Hz, 3H). $^{13}$C NMR (100 MHz, CDCl$_3$): δ 205.6, 173.0, 79.2, 61.8, 47.3, 43.5, 30.3, 22.1, 13.9. ESI-HRMS: calcd for C$_9$H$_{16}$O$_5$N ([M+H]$^+$) 218.1028, found 218.1004.

Example 7

Transformations to Pyrrolidines

[Chem. 80]

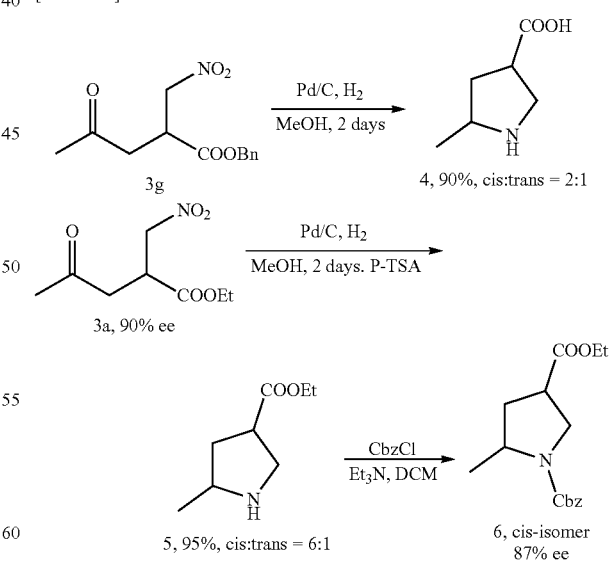

Transformation 3g to 4

Compound 3g (190 mg) was dissolved in anhydrous MeOH (10 mL) and 10% Pd/C (143 mg) was added. The mixture was stirred under a H$_2$ balloon for 2 days at room temperature. The mixture was filtered through celite and the filtrate was concentrated under vacuum to afford 4 (83.3 mg, 90%).

(3R,5S)-5-methylpyrrolidine-3-carboxylic acid

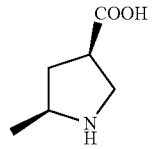

[Chem.81]

<Chemical Data>

Colorless solid. $^1$H NMR (400 MHz, CD$_3$OD): δ 3.29-3.22 (m, 1H), 3.21-3.10 (m, 1H), 3.07-2.97 (m, 1H), 2.95-2.83 (m, 1H), 2.34-2.20 (m, 1H), 1.61-1.49 (m, 1H), 1.26 (d, J=6.4 Hz, 3H). $^{13}$C NMR (100 MHz, CD3OD): δ 182.8, 57.1, 51.2, 48.6, 40.1, 19.3.

Transformation 3a to 6

Compound 3a (203 mg) was dissolved in anhydrous MeOH (10 mL) and 10% Pd—C (173 mg) and p-TSA (187 mg) were added. The mixture was stirred under a H$_2$ balloon for 2 days at room temperature. The mixture was filtered through celite and the filtrate was concentrated under vacuum to afford 5 (p-TSA salt).

To a solution of 5 (p-TSA salt) in CH$_2$Cl$_2$ (20 mL), triethylamine (530 μL) was added dropwise. After 30 min, benzyl chloroformate (270 μL) was added dropwise and the mixture was stirred for 10 h at room temperature. The mixture was treated with saturated aqueous NaHCO$_3$ (20 mL) and extracted with CH$_2$Cl$_2$. Organic layers were combined, washed with brine, dried over Na$_2$SO$_4$, concentrated, and purified by flash column chromatography (hexane/EtOAc=2:1) to afford 6.

(3R,5S)-1-((benzyloxy)carbonyl)-5-methylpyrrolidine-3-carboxylic acid ethyl ester

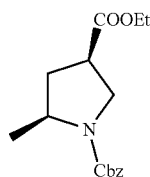

[Chem. 82]

<Chemical Data>

Colorless oil. $^1$H NMR (400 MHz, CDCl$_3$): δ 7.49-7.28 (m, 5H), 5.24-5.03 (m, 2H), 4.16 (q, J=7.1 Hz, 2H), 4.04-3.77 (m, 2H), 3.64-3.52 (m, 1H), 3.03-2.88 (m, 1H), 2.49-2.33 (m, 2H), 2.02-1.77 (m, 1H), 1.43-1.14 (m, 6H). $^{13}$C NMR (100 MHz, CDCl$_3$): δ 172.8, 154.5, 136.8, 128.5, 128.0, 127.9, 66.7, 61.0, 53.7, 48.2, 42.3, 36.6, 20.2, 14.1. ESI-HRMS: calcd for C$_{16}$H$_{22}$O$_4$N ([M+H]$^+$) 292.1543, found 292.1536.

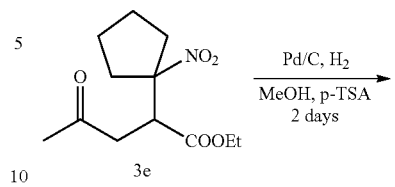

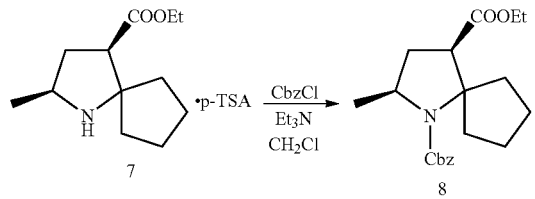

Transformation 3e to 8

Compound 3e (115.0 mg, 0.447 mmol) was dissolved in anhydrous MeOH (10 mL), 10% Pd on charcoal (62.0 mg) and p-toluenesulfonic acid (p-TSA) (91.4 mg) were added. The mixture was stirred under a H$_2$ balloon for 2 days at room temperature. The mixture was filtered through celite and the filtrate was concentrated under vacuum to afford 7 (p-TSA salt). The yield was determined to be 50% by the NMR analysis using CH$_2$Br$_2$ as an internal standard that was added to the solution of 7 (p-TSA salt).

To a solution of 7 (p-TSA salt) in CH$_2$Cl$_2$ (20 mL), triethylamine (226 μL) was added dropwise. After 30 min, benzyl chloroformate (115.5 μL) was added dropwise and the mixture was stirred for 10 h at room temperature. The mixture was treated with saturated solution of aqueous NaHCO$_3$ (20 mL) and extracted with CH$_2$Cl$_2$. Organic layers were combined, dried over anhydrous Na$_2$SO$_4$, concentrated, and purified by flash column chromatography (hexane/EA=2:1) to afford 8.

(2S,4R)-1-benzyl 4-ethyl 2-methyl-1-azaspiro[4.4]nonane-1,4-dicarboxylate

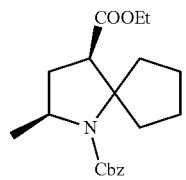

[Chem. 84]

<Chemical Data>

Colorless oil. $^1$H NMR (400 MHz, CDCl$_3$): δ 7.45-7.28 (m, 5H), 5.23-5.05 (m, 2H), 4.26-4.06 (m, 2H), 3.93-3.82 (m, 1H), 2.86-2.71 (m, 1H), 2.27-2.12 (m, 1H), 2.03-1.67 (m, 6H), 1.44-1.00 (m, 9H). $^{13}$C NMR (100 MHz, CDCl$_3$): δ 171.7, 153.8, 136.7, 128.4, 128.1, 128.0, 73.4, 66.4, 60.7, 54.2, 53.3, 35.4, 34.4, 29.7, 26.9, 25.5, 22.6, 14.1.

Benzyl 5-methylpyrrolidine-3-carboxylate

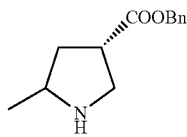
[Chem. 85]

<Procedure>
Synthesized according to preparation in Example 6, by using compound 3g.

Ethyl 5-ethylpyrrolidine-3-carboxylate

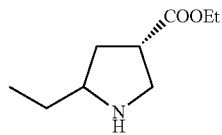
[Chem. 86]

<Procedure>
Synthesized according to preparation in Example 7, by using compound 3i.

Ethyl 5-isopropylpyrrolidine-3-carboxylate

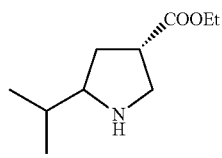
[Chem. 87]

<Procedure>
Synthesized according to preparation of compound 3a, by ethyl 5-methyl-4-oxohex-2-enoate instead of ethyl 4-oxo-pent-2-enoate by Michael reaction, and preparation in Example 7.

INDUSTRIAL APPLICABILITY

The present invention can provide a novel chemically and biologically important 3-pyrrolidine carboxylic acid derivative and a highly-stereoselective, moderate, atom economic process for preparing 3-pyrrolidine carboxylic acid derivatives.

The invention claimed is:
1. A process for preparing compound of formula I':

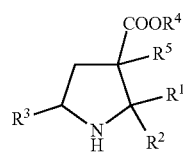

wherein
R$^1$ and R$^2$ are each independently hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl; or
R$^1$ and R$^2$ together form —(CH$_2$)$_n$—, and n is 2 to 6;
R$^3$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl;
R$^4$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl; and
R$^5$ is hydrogen, C$_{1-7}$-alkyl, C$_{3-7}$-cycloalkyl, halo-C$_{1-7}$-alkyl, C$_{1-7}$-alkoxy-C$_{1-7}$-alkyl, aryl-C$_{1-7}$-alkyl, or heteroaryl-C$_{1-7}$-alkyl;
or a pharmaceutically acceptable salt thereof, which process comprises
step A: reacting compound of formula II:

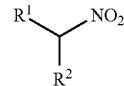

wherein R$^1$ and R$^2$ are as defined above, with compound of formula III:

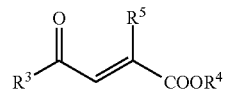

wherein R$^3$, R$^4$ and R$^5$ are as defined above, in the presence of at least one of compound X which is selected from the group consisting of:

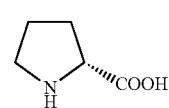
A

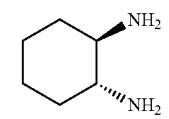
B

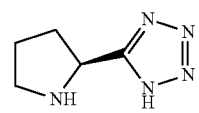
C

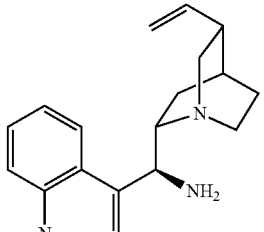
D

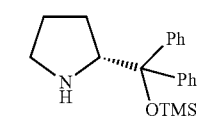
E

-continued
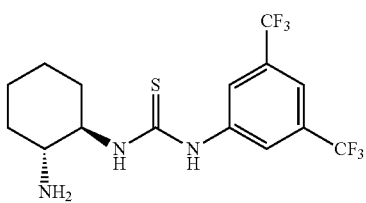
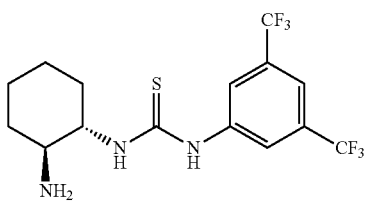
to obtain compound of formula IV:
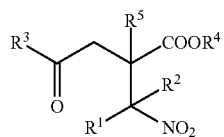
wherein $R^1$, $R^2$, $R^3$, $R^4$, and $R^5$ are as defined above,
step B: reacting compound of formula IV with a reductant to obtain compound of formula I'.
2. The process according to claim 1, wherein the reductant is zinc and acetic acid, or Pd/C and hydrogen.
* * * * *